(12) United States Patent
Gao

(10) Patent No.: US 8,573,961 B2
(45) Date of Patent: Nov. 5, 2013

(54) MOLD FOR MANUFACTURING A FOLDABLE ARTIFICIAL VITREOUS BODY

(75) Inventor: Qianying Gao, Guangzhou (CN)

(73) Assignee: Guangzhou Vesber Biotechnology Co., Ltd, Guangzhou (CN)

( * ) Notice: Subject to any disclaimer, the term of this patent is extended or adjusted under 35 U.S.C. 154(b) by 0 days.

(21) Appl. No.: 13/565,175

(22) Filed: Aug. 2, 2012

(65) Prior Publication Data

US 2012/0301566 A1  Nov. 29, 2012

Related U.S. Application Data

(60) Division of application No. 12/841,667, filed on Jul. 22, 2010, now Pat. No. 8,419,994, which is a continuation of application No. PCT/CN2009/000336, filed on Mar. 30, 2009.

(30) Foreign Application Priority Data

Oct. 15, 2008 (CN) .......................... 2008 1 0199177

(51) Int. Cl.
*B29C 45/26* (2006.01)
(52) U.S. Cl.
USPC ......... 425/185; 425/190; 425/192 R; 425/577
(58) Field of Classification Search
USPC ...................... 425/182, 185, 190, 192 R, 577
See application file for complete search history.

(56) References Cited

U.S. PATENT DOCUMENTS

| | | | | |
|---|---|---|---|---|
| 4,202,522 A | * | 5/1980 | Hanas et al. | 425/185 |
| 4,775,130 A | * | 10/1988 | Von Holdt | 425/577 |
| 4,902,292 A | | 2/1990 | Joseph | |
| 5,091,121 A | | 2/1992 | Nakada et al. | |
| 5,376,323 A | | 12/1994 | Eaton | |
| 6,939,486 B2 | | 9/2005 | DeRyke et al. | |
| 7,794,223 B2 | * | 9/2010 | Kuo | 425/190 |

(Continued)

FOREIGN PATENT DOCUMENTS

| | | |
|---|---|---|
| CN | 14833388 | 3/2004 |
| CN | 2647270 | 10/2004 |
| CN | 1810301 | 8/2006 |
| CN | 101386203 | 3/2009 |

OTHER PUBLICATIONS

International Search Report of PCT/CN2009/000336 mailed Jul. 23, 2009 (6 pages total).

*Primary Examiner* — Tim Heitbrink
(74) *Attorney, Agent, or Firm* — Hamre, Schumann, Mueller & Larson, P.C.

(57) ABSTRACT

The present invention relates to a foldable capsular vitreous body (FCVB), and its mold design, method for manufacturing, product appearance, and drug delivery property and so on. A mold for molding a foldable artificial vitreous body comprises an upper mold (1), a lower mold (2) and a core (3). The core (3) is disposed between the upper mold (1) and the lower mold (2) and is connected with a drainage-tube pin connected with an injection channel (4). Heating holes (6) are disposed in the upper mold (1) and/or the lower mold (2). Material is injected to the mold and is heated to vulcanize to mold vitreous body. The FCVB is adapted to be injected with any harmless medium and can be used as a delivery vehicle inside or around the eye ball. The size or shape of the FCVB can be changed depending on the different implant site.

5 Claims, 3 Drawing Sheets

(56) References Cited

U.S. PATENT DOCUMENTS

| | | |
|---|---|---|
| 7,879,088 B2 | 2/2011 | Gao et al. |
| 7,914,274 B2 * | 3/2011 | Huang ...................... 425/192 R |
| 7,922,472 B2 * | 4/2011 | Kuo .............................. 425/190 |
| 8,167,941 B2 | 5/2012 | Boyd et al. |
| 2007/0173933 A1 | 7/2007 | Gao et al. |
| 2008/0125862 A1 | 5/2008 | Blake |

* cited by examiner

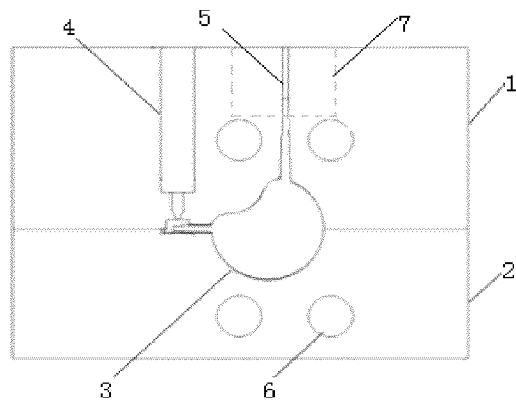
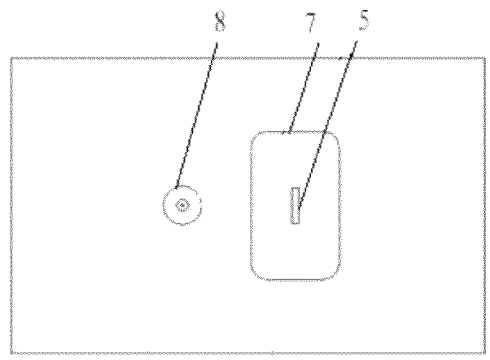
Fig. 1                     Fig. 2
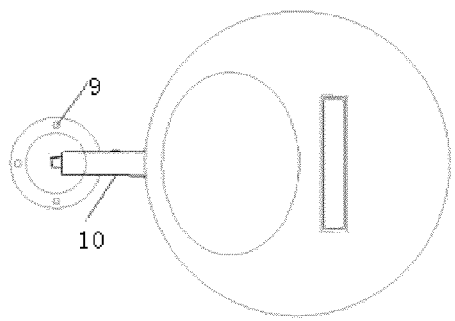
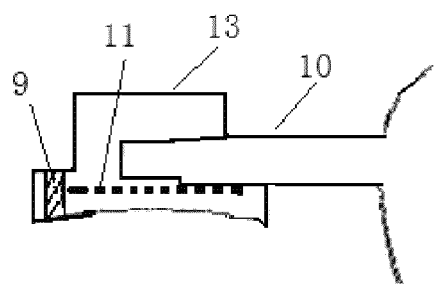
Fig. 3                     Fig. 4
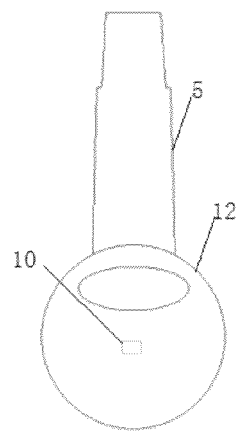
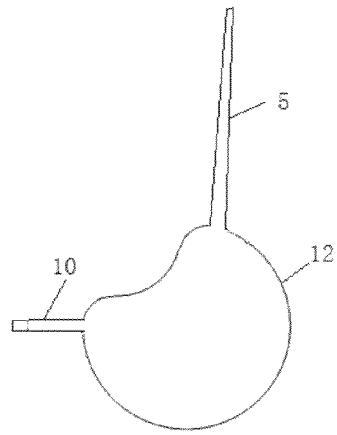
Fig. 5a                    Fig. 5b

MOLD FOR MANUFACTURING A FOLDABLE ARTIFICIAL VITREOUS BODY

This application is a Divisional of application Ser. No. 12/841,667, filed Jul. 22, 2010, now U.S. Pat. No. 8,419,994 which is a Continuation of PCT/CN2009/000336, filed Mar. 30, 2009, which applications are incorporated herein by reference.

FIELD OF THE INVENTION

The present invention relates to a foldable capsular vitreous body, and its mould design, method for manufacturing, product appearance, drug delivery property, surgical applications, and so on.

BACKGROUND OF THE INVENTION

Currently, national and international studies on substitutes for vitreous body are numerous, mainly including inert gas, silicone oil, heavy silicone oil, perfluorocarbon liquids, and hydrogels composed of high molecular weight hydrophilic polymers being the national or international research focus in the 1990s. However, their therapy results are not satisfying, some of which could result in serious complications, for example, inert gas for instance C3F8 may cause cataract easily and lose the effect of tamponade at about two weeks after the surgery such that it could not generate sustained top-pressure on the retina; Perfluorocarbon liquids is toxic to the retina such that it could not settle in the cavity of vitreous body for a long time and could be utilized in surgery only. Additionally, perfluorocarbon liquids is easy to remain in the eyes and difficult to remove after reaction with water. Present substitutes for silicon oils widely used in clinic could result in glaucoma and cataract and will self-emulsify within a particular time. The emulsified substitutes had to be removed. However, upon removing, the retina is easy to detach again. Repetitive surgeries not only aggravated the burden of patients but also seriously impaired the vision of the patients; Even though the surgery is successful, the vision of the patients is very poor resulting from that low refractive index of silicon oil could not generate adequate top pressure on the breaks underlying the retina, and that the diopter in eyeball shifted to high hyperopia after filling; Additionally, after surgeries, patients had to lie on stomach for a long time to prevent silicon oil from flowing into the anterior chamber, thus making the patients very agonized. Hydrogels mainly included PVP hydrgels, PVA hydrogels, PAM hydrogels and Poly (1-vinyl-2-pyrrolidone) hydrogels, and so on. However, these hydrogels are still at the experimental stage in ophthalmology, and so far no one of these hydrogels is performed in clinic application resulting in lack of observation on the long-term therapeutic effect on the toxicity to the eyes and the price is very high. The patients could not afford it. Finding out vitreous substitutes which met physiological needs and are more economical is required, which is one of problems disturbing the doctors for vitreous retinal disorders in the century.

How to make an artificial vitreous body of which both structure and function are the same as those of the natural vitreous body is one of the keys to ensure the success of vitrectomy. Up to now, the components of vitreous body are not fully known. Based on the conditions of modern science and technology, the need to make an artificial vitreous body of which both structure and function are perfect is impractical. The current substitutes for vitreous body are sometimes called as artificial vitreous body. Implantation methods are performed by directly injecting the substitutes for vitreous body into the cavity of vitreous body to support the retina to prevent the retina from detaching again.

Therefore, without pursuing to make a fully physiological artificial vitreous body, the research thinking is changed to restore the most important function of vitreous body, i.e. support of retina so as to avoid repetitive retinal detachment, which is also a method to resolve the problem. Here we design a novel therapy method as using foldable capsular vitreous body (FCVB) to substitute the natural vitreous body. The FCVB consist of a thin capsule, drainage tube and valve. And it also equipped with auxiliary tools: the ejector handle. Chinese Patent No. ZL 03126845.5 discloses a technical scheme and manufacture method for FCVB. Chinese Patent Publication No. CN1810301 (A) and US Patent Publication No. US2007173933 (A1) further limit the material and manufacturing process (dip-molding) of FCVB. The present patent application further extends the material and another manufacturing process of FCVB. New mould design method and capsule pressure regulating drainage valve are added.

SUMMARY OF THE INVENTION

The object of the present invention is to provide a foldable capsular vitreous body (FCVB) for artificial vitreous body with high biocompatibility and excellent flexibility, advanced and stable technology. The invention also provides a capsule pressure regulating drainage valve, the manufacturing process and the mould thereof.

The object of the present invention is carried out as follows:

A mould for the manufacture of FCVB includes three major parts, an upper mould, a lower mould, and a core between these two moulds. A drainage tube pin is connected to the core and to the plastic injection channel. Heating holes are provided on the upper mould and/or the lower mould. The mold is further connected to a temperature control equipment to control the manufacture to be carried out within a suitable temperature.

The upper mould has a slide block, the core is connected to a positioning plate, and the positioning plate can be positioned in the slide block. The principal axis of the positioning plate is at right angle with respect to the principal axis of the drainage tube pin, the positioning plate and the centre of the core are on the same plane. The drainage tube pin is connected with the drainage valve via the plastic injection channel.

The invention also provides a method using the mould above to manufacture the FCVB. Materials are injected into the mould and vulcanized to form the FCVB. The method including following steps:

(1) mixing evenly natural or modified macromolecule materials, vacuumizing and setting aside;

(2) coating a proper amount of processing materials on the drainage valve and laying a rigid sheet;

(3) putting the core between the upper mould and the lower mould, closing and locking the mould;

(4) injecting the processing materials obtained in the step (1) into the mould cavity from the plastic injection channel;

(5) heating the mould via the heating holes and solidifying the material in the mould cavity;

(6) opening the mould, taking out the core after cooling, and peeling out the capsular bag.

To extend the life of the mould and to prepare for the next manufacturing, the mould must be cleaned each time after the products are stripped out.

The capsular bag for FCVB is mainly made of one selected from the group consisting of polysiloxane, polyurethane, styrene triblock copolymer thermoplastic elastomers, hydroxyethyl methacrylate (HEMA), polyvinyl alcohol (PVA), poly (lactide-co-glycolide) (PLGA) and hyaluronic acid ester.

As an improvement to the present invention, materials of the FCVB, such as polysiloxane or polyurethane are modified by adding hydroxy (—OH)-containing hydrophilic groups, to control water rate in the capsular bag such that the water rate is 5-30%; fluoro group-containing materials are added into the materials of polysiloxane or polyurethane to increase oxygen permeability of the capsular bag.

Preferably, the materials are absorbable materials, so that the implanting FCVB will be absorbed slowly over disease treatment period, to avoid secondary removal of the foldable intraocular vitreous body. Dilution is added into the processing material to alter the physical state of the processing materials. Volatile dilution is preferable, in order to enable the natural volatilization.

In the step (2), by coating a proper amount of processing materials on the drainage valve and fixing on a rigid sheet, the rigid sheet prevents the FCVB from being perforated by the injector pins to ensure the gas-tightness of the body. When artificial plastic injection approach is used, a proper amount of materials may be pre-coated on the upper and lower molds.

After the step (6), the obtained capsule can be further processed: a proper amount of processing materials is coated on the peeling opening of the capsular bag, then put the capsular bag in a sealing device which matches with the peeling opening of the capsular bag to realize the post forming of the peeling opening, and trim the peeling opening by trimmer after agglutination. The operating temperature of the sealing device is in a range of 60° C.-300° C., preferably at 110° C., with working time of more than 2 seconds, preferably 6 seconds.

The capsule products obtained in the step (6) may be processed by the following process:

a proper amount of diluted processing materials is coated on the peeling opening of the capsular bag obtained in the step (6), then the peeling opening of the capsular bag is vulcanized and sealed by heating with an infrared lamp; or a proper amount of room temperature solidified gel materials is coated to seal the peeling opening directly as the gel materials solidified in room temperature.

In the step (5), the heating temperature is controlled in a range of 80° C.-300° C., and preferably at 160° C.

In the method for manufacturing a foldable artificial vitreous body, the permeability of capsular bag is controlled by changing the aperture, wall thickness of capsular bag, osmotic pressure of medium in capsular bag or using nanotechnology, and therapeutic drug, nutritional factors or natural vitreous effective composition are injected via the drainage valve to make the capsular bag product to become a sustained drug deliver system (DDS).

The manufacture method allows batch production of the FCVB by connecting multiple cores with the plastic injection channel simultaneously.

The invention also provides a FCVB produced by the manufacturing method and manufacturing mould as described above. The FCVB includes a capsule, a drainage tube and a drainage valve. The drainage tube has an inner opening and an outer opening connected to the capsule and the drainage valve respectively, and a small recess is provided on the capsule.

The bottom of the drainage valve has the same curvature as the ocular surface. A rigid sheet is disposed at the bottom of the valve to prevent it from being pierced and to maintain its air tightness. Actually, the valve is still air tightness after puncturing for many times. The valve has cracks to regulate the pressure inside the capsule. The valve can be in any shape such as triangular, trapezoidal, rectangular or irregular shape.

The FCVB can be used as a drug delivery system (DDS) inside or around the eye ball, such as eye wall, retrobulbar, peribulbar, eye muscle, orbital wall, by injecting therapeutic drugs, nutritional factors, biological agents, cell, radioisotope, makers, natural active ingredients of vitreous body and so on, which could cure eye diseases including ametropia, uveitis, ocular tumors, degenerative eye diseases, vascular disease, optic neuropathy and so on.

The size or shape of the FCVB can be changed depending on the different implant site. The shape including circle, fan, oval, triangle, quadrilateral, trapezoid, polygon, tubular, sphere, ellipsoid, cylindrical, ring, semi-ring and so on.

Some harmless medium such as physiological saline, silicone oil, heavy silicone oil, hydrogel, can be injected into the FCVB, and the fluid is in liquid or gel state after injection.

The FCVB can also be used as an orbital implant.

Comparison of current technologies, the invention has the following advantages:

(1) Safety with low toxicity. Since restricted by the capsule, the substitutes for vitreous body are not in comprehensive contact with the ophthalmic tissues, thus avoiding the effect of current substitutes for vitreous body on anterior segment. The capsule is easy to be removed completely. Even the patient could not endure the serious reaction in eyes, it could be removed easily, and thus avoiding the current substitutes for vitreous body remaining in the eyes due to difficult removing.

(2) Good result of top pressure on the retina. Because expanding evenly, the capsule could generate sustained top pressure on retinal breaks in any position so as to decrease the recrudescent chances of retinal detachment and increase the cure rate of the operation, which largely alleviated the patients' financial burden due to avoiding repetitive operations;

(3) The drainage valve of FCVB can control the pressure inside the capsule, and to avoid the frequent optic nerve damages caused by high intraocular pressure.

(4) The post Operative visual acuity is better. As the optical parameters of the FCVB are closer to the normal vitreous body, so the patients will gain better vision.

(5) The FCVB is skillfully integrated with the sustained drug release system. By controlling the permeability of the capsule, a DDS is formed to control the sustained release result of the FCVB. Treatment of eye disease or eye nutrition can be achieve by injecting therapeutic drugs, nutritional factors, biological agents, cell, radioisotope, makers, natural active ingredients of vitreous body and so on.

(6) There are lots of differences in comparison with the previous patents (Chinese Patent No. ZL 03247199.8, Chinese Patent No. ZL 03126845.5), such as basic materials, manufacturing method, mold design and drainage valve.

| | Patent No. | | |
|---|---|---|---|
| differences | ZL 03126845.5 | ZL 03247199.8 | the present invention |
| Manufacturing technology | Manual method | Dip molding | Injection molding |
| Basic materials | Acetic acid and vinyl acetate copolymer | Polysiloxane elastomer, etc. | Polysiloxane elastomer, etc. |

-continued

| differences | Patent No. ZL 03126845.5 | ZL 03247199.8 | the present invention |
|---|---|---|---|
| Manufacturing method | Handwork | Die dipped, hardened to shape. The capsular, drainage tube and valve are not formed within one procedure. The wall of tube is thick. | Injection molding. Capsular, drainage tube and valve are formed within one procedure. The wall of tube is soft. Good integrity and less damage to eyes. |
| Mold design | No | Capsule and valve are form by two mould sets. Data of the die are different to the physiological parameters of human eye. | The mould consists of the upper and lower mould, and the core. Parameters of the mould are according to the physiological parameters of human eye. Equipped with pressure control, heating, cooling and temperature control equipments |
| Drainage valve. | Greater size and hardness | Greater size and hardness | Small, soft, and good biocompatibility; Possess pressure-sensitive valve and locative hole |
| Delivery vehicle | No | Intraocular drug delivery system | Be used as a delivery vehicle inside or around the eye ball by injected harmless medium such as therapeutic drugs, nutritional factors, biological agents, cell, radioisotope, makers, natural active ingredients of vitreous body, physiological saline, silicone oil, heavy silicone oil, hydrogel and so on. |

BRIEF DESCRIPTION OF THE DRAWINGS

FIG. 1 is a schematic cross-sectional view of a mold according to an embodiment of the present invention;

FIG. 2 is a top view of the mold;

FIG. 3 is a top view of the drainage valve of the mold;

FIG. 4 is a lateral view of the drainage valve of the mold;

FIGS. 5a and 5b are schematic views of the core of the mold;

DETAILED DESCRIPTION OF THE PREFERRED EMBODIMENT

Figure 6:
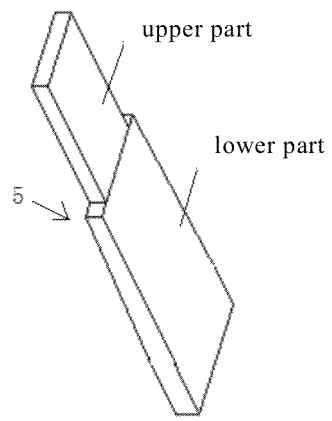
FIG. 6 is a schematic view of the positioning plate of the mold.

Referring to FIGS. 1-4, the mold in this embodiment comprises the upper mould 1, the lower mould 2, and the core 3. The core 3 which is connected with the drainage tube pin 10, is set between the upper mould 1 and the lower mould 2, the drainage tube pin 10 is connected with plastic injection channel 4). Heating holes 6 are provided on the upper mould 1 and the lower mould 2.

The upper mould 1 has a slide block 7, and the core 3 is connected with the positioning plate 5 which located in the slide block 7. The drainage tube pin 10 is connected with the plastic injection channel 4 via the drainage valve 13.

Referring to FIGS. 5 and 6, the core 3 is connected with the positioning plate 5 which includes an upper part and a lower part, and the upper part is fixed in the slide block 7.

The drainage tube pin 10 is connected with the plastic injection channel 4 via the drain valve 13, the drain valve has a piece of rigid sheet which is positioned by the located pin 9. An aluminum sheet 11 is used in this embodiment.

The method for manufacturing FCVB is performed with above mentioned mold, comprising the following steps:

(1) mixing evenly natural or modified macromolecule materials, vacuumizing and setting aside;

(2) coating a proper amount of processing materials on the drainage valve and laying a rigid sheet;

(3) putting the core between the upper mould and the lower mould, closing and locking the mould;

(4) injecting the processing materials obtained in the step (1) into the mould cavity from the plastic injection channel;

(5) heating the mould via the heating holes and solidifying the material in the mould cavity;

(6) opening the mould, taking out the core after cooling, and peeling out the capsular bag;

(7) cleaning the mould;

(8) a proper amount of processing materials is coated on the peeling opening of the capsular bag, then put the capsular bag in a sealing device which matches with the peeling opening of the capsular bag to realize the post forming of the peeling opening.

In detail, the steps are as follows:

1. Mix evenly natural or modified macromolecule materials, vacuumize and set aside;

2. Coat a proper amount of processing materials on the drainage valve, and lay a rigid sheet; if the materials are injected manually, a proper amount of processing materials is pre-coated on the upper and lower moulds; and if the materials are injected mechanically, then a proper amount of the processing materials may not be coated.

3. Put the core between the upper mould and the lower mould, and a) if the materials are injected manually, a proper amount of processing materials is pre-injected into the plastic injection channel to dispel the air in the plastic injection channel, and then close and lock the mould to start the injection; and b) if the materials are injected mechanically, after assemble and lock the mold, vacuumize the mold (the clamping force is 0-100N) to exhaust the air in the mould, and then inject the materials into the mould through the plastic injection channel.

4. Heat the mould to a temperature in a range of 80° C.-300° C., and to 160° C. in this embodiment. Then, open and cool the mould, take out the core and remove the FCVB.

5. Clean up the mould.

6. A proper amount of processing materials is coated on the peeling opening of the capsular bag, then put the capsular bag in a sealing device which matches with the peeling opening of the capsular bag to realize the post forming of the peeling opening. The operating temperature of the sealing device is in a range of 60° C.-300° C., and at 110° C. in this embodiment, with working time more than 2 seconds and about 6 seconds in this embodiment.

7. A trimmer is used to trim the peeling opening after agglutination.

8. Cool the mould to the room temperature (<30° C.) (possible range <100° C.) and then fabricate the next FCVB.

Figure 7:
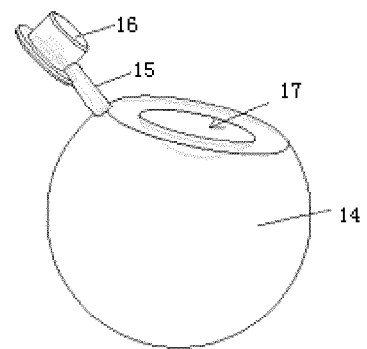
FIG. 7 is a schematic view of a FCVB in the present invention.

As show in FIG. 7, the FCVB obtained by using the manufacturing methods and the mould described above, comprises the capsular bag 14, the drainage tube 15 and the drain valve 16. The capsular bag 14 is connected with the drain valve 16 via the drainage tube 15. A small recess 17 is formed on the capsular bag 14.

Referring to FIG. 4, the bottom of drainage valve 16 has the same curvature with the ocular surface. An aluminum sheet 11 is embedded at the bottom of the valve 16 to prevent it from being pierced and to maintain its air tightness. Actually, the valve is still air tightness after being punctured for many times. The valve has cracks to regulate the pressure inside the capsule. The valve can be in any shape such as triangular, trapezoidal, rectangular or irregular shapes.

The FCVB has an anteroposterior diameter of 5-40 mm and a vertical diameter of 10-40 mm, and a recess with curvature radius of 1-20 mm and chord length of 1-40 mm.

The wall thickness of the capsular bag for FCVB is 0.01-1 mm; Shore hardness of the capsular bag is in a range of 5-40 degree; the tensile strength is in a range of 4-12 Mpa; the hemolysis rate of material is not more than 5%; the transmission rate is not less than 90%; the fog density is not more than 0.1%; the elongation is not less than 500%; and the tear strength is in a range of 10-40 kN/m.

The drainage tube has a length of 2-15 mm, an outer diameter of 0.1-10 mm and an inner diameter of 0.1-10 mm, and the vertical distance of the inner opening of the drainage tube is 2-20 mm from principal axis. The drainage tube may be a straight tube or curved in any shape.

The drainage valve has a bigger end with an external diameter of 2-20 mm and a smaller end with an external diameter of 1-20 mm, and has a total thickness of 1-10 mm, the thickness on puncturing portion of 1-10 mm, positioning holes with diameter of 0.1-5 mm and depth of 0-10 mm. The size or shape of the FCVB depends on the different implant site.

The FCVB is able to be used as a drug delivery system inside or around the ocular, by injecting therapeutic drugs, nutritional factors, natural active ingredients of vitreous body and so on. According to the different implant site, the size or shape of the FCVB corresponding varies. Any harmless fluid can be injected into the FCVB, and is in liquid or gel state after injection.

Figure 8:
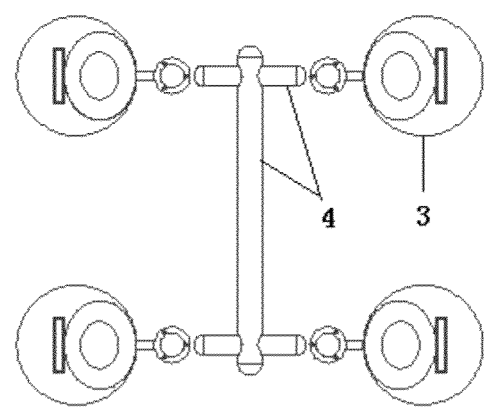
FIG. 8 is a schematic view of a mold with multiple cores for batch production of the FCVB.

In FIG. 8, a schematic view of a mold with multiple cores for batch production of the FCVB is shown. The plastic injection channel 4 is connected with multiple cores, so that the materials can be injected into the mould through the plastic injection channel to realize the batch production.

Figures 9A, 9B:
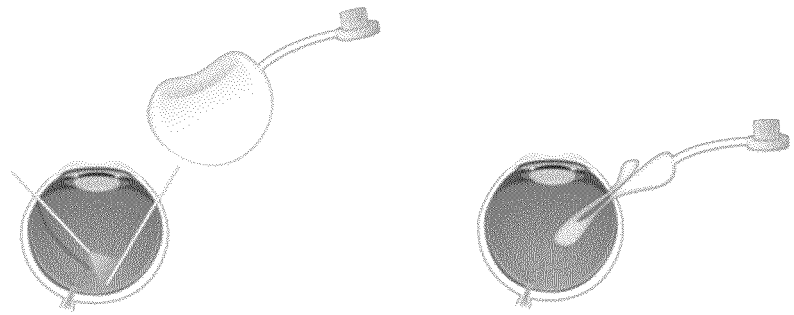
FIGS. 9a-9d are schematic views showing the process of the implantation of the FCVB into the eye.
Figures 9C, 9D:
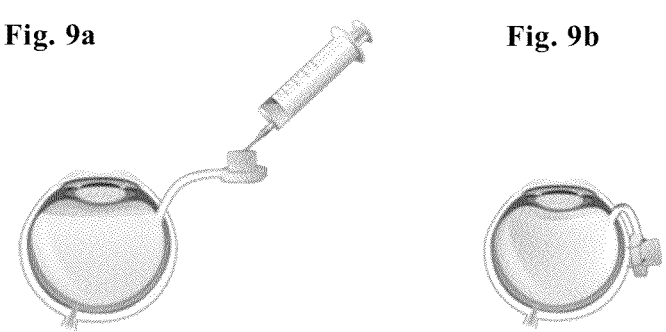

FIGS. 9a to 9d show the surgery operation in implanting the FCVB. In FIGS. 9a and 9b, the FCVB is folded and implanted in to the vitreous cavity. In FIG. 9c, the solution is injected into the capsule through the tube-valve system. In FIG. 9d, the tube and the valve are subsequently fixed under the conjunctiva.

Figure 10:
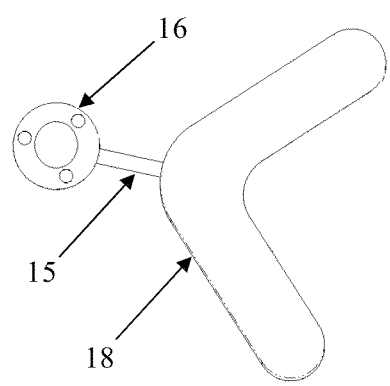
FIG. 10 is a schematic view of a FCVB used as a delivery vehicle inside or around the eye ball in the present invention.

FIG. 10 is a schematic view of a FCVB used as a delivery vehicle inside or around the eye ball in the present invention. The FCVB can be used as a drug delivery system (DDS) inside or around the eye ball, such as eye wall, retrobulbar, peribulbar, eye muscle, orbital wall, by injected therapeutic drugs, nutritional factors, biological agents, cell, radioisotope, makers, natural active ingredients of vitreous body and so on, which could cure eye diseases including ametropia, uveitis, ocular tumors, degenerative eye diseases, vascular disease, optic neuropathy and so on.

The size or shape of the FCVB can be changed depending on the different implant site. The shape of the capsular bag 18 including circle, fan, oval, triangle, quadrilateral, trapezoid, polygon, tubular, sphere, ellipsoid, cylindrical, ring, semi-ring and so on.

Some harmless medium such as physiological saline, silicone oil, heavy silicone oil, hydrogel, can be injected into the FCVB, and the fluid is in liquid or gel state after injection.

It should be emphasized that the above-described embodiments of the present invention, particularly, any preferred embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

What is claimed is:

1. A mould for manufacturing a foldable artificial vitreous body, comprising:
   an upper mould;
   a lower mould; and
   a core disposed between the upper mould and the lower mould, and connected with a drainage tube pin;
   wherein the drainage tube pin is connected with a plastic injection channel, and heating holes are provided on the upper mould and/or the lower mould.

2. The mould according to claim 1, wherein the upper mould has a slide block, and the core is connected with a positioning plate which is located in the slide block.

3. The mould according to claim 2, wherein the principal axis of the positioning plate is at right angle with respect to the principal axis of the drainage tube pin, the positioning plate and the centre of the core are on the same plane.

4. The mould according to claim 1, wherein the drainage tube pin is connected with the plastic injection channel via a drainage valve.

5. The mould according to claim 1, wherein the mould is further connected with a temperature control equipment.

* * * * *